United States Patent
Xia et al.

(10) Patent No.: US 12,268,782 B2
(45) Date of Patent: Apr. 8, 2025

(54) PREPARATION METHOD OF FATTY ACID LIPOSOME FOR VC ENCAPSULATION

(71) Applicant: Jiangnan University, Wuxi (CN)

(72) Inventors: Yongmei Xia, Wuxi (CN); Huan Liu, Wuxi (CN); Xinyu Meng, Wuxi (CN); Yun Fang, Wuxi (CN); Ye Fan, Wuxi (CN); Jie Shen, Wuxi (CN); Xiang Liu, Wuxi (CN)

(73) Assignee: Jiangnan University, Wuxi (CN)

( * ) Notice: Subject to any disclaimer, the term of this patent is extended or adjusted under 35 U.S.C. 154(b) by 518 days.

(21) Appl. No.: 17/685,476

(22) Filed: Mar. 3, 2022

(65) Prior Publication Data
US 2022/0183974 A1 Jun. 16, 2022

Related U.S. Application Data

(63) Continuation of application No. PCT/CN2021/098057, filed on Jun. 3, 2021.

(30) Foreign Application Priority Data

Jun. 4, 2020 (CN) .......................... 202010497171.5

(51) Int. Cl.
*A61K 9/1278* (2025.01)
*A61K 8/14* (2006.01)
*A61K 31/375* (2006.01)
*A61P 3/02* (2006.01)
*A61Q 19/00* (2006.01)

(52) U.S. Cl.
CPC .............. *A61K 9/1278* (2013.01); *A61K 8/14* (2013.01); *A61K 31/375* (2013.01); *A61P 3/02* (2018.01); *A61Q 19/00* (2013.01)

(58) Field of Classification Search
CPC ...... A61K 9/1278; A61K 8/14; A61K 31/375; A61K 8/676; A61P 3/02; A61Q 19/00
See application file for complete search history.

(56) References Cited

FOREIGN PATENT DOCUMENTS

| CN | 103386132 A | 11/2013 |
|---|---|---|
| CN | 107998978 A | 5/2018 |

(Continued)

OTHER PUBLICATIONS

Maranasco et al. Food Research International 44 (2011) 3039-3046 (Year: 2011).*

(Continued)

*Primary Examiner* — Carlos A Azpuru
(74) *Attorney, Agent, or Firm* — IPRO, PLLC

(57) ABSTRACT

The present disclosure discloses a preparation method of fatty acid-based VC liposomes, and belongs to the field of pharmaceutical preparations. In the disclosure, a complex of industrial conjugated linoleic acid and other fatty acids with sodium dodecyl sulfate is taken as a capsule material, which is self-assembled to embed vitamin C in an aqueous phase under an acidic condition (pH<7) to form the fatty acid-based vitamin C liposome. The preparation method of the disclosure does not use organic solvents and other substances harmful to the human body, and has the characteristics of safety and health. In addition to VC encapsulation under the acidic condition, the prepared fatty acid-based liposome can play a role in slowly releasing VC.

7 Claims, 2 Drawing Sheets

(56) References Cited

FOREIGN PATENT DOCUMENTS

| | | |
|---|---|---|
| CN | 111557912 A | 8/2020 |
| JP | 2006225327 A | 8/2006 |

OTHER PUBLICATIONS

Christie et al. JAOCS, vol. 74, No. 11 (1997) (Year: 1997).*

Ikari et al. Soft Matter, 2015, 11, 6327 (Year: 2015).*

Yang Shuibing et al., "Preparation and Characterization of Nanoliposomes Entrapping Medium-Chain Fatty Acids and Vitamin C by Lyophilization ", Int. J. Mol. Sci. ,V14, Sep. 30, 2013.

Ma, Jle "The investigation of migration and extension of pH window for forming conjugted linoleic acid ufasomes, China Excellent Doctoral and Master" s Thesis Full-text Database (Master) Engineering Science and Technology vol. 1, Issue 12, Dec. 15, 2015.

Fan, Ye et al., "Neutral and acid-adapted fatty acid vesicles of conjugated linoleic acid", Colloids and Surfaces B: Biointerfaces, V167,Apr. 20, 2018.

Davis Janelle L. et.al, "Liposomal-encapsulated Ascorbic Acid: Influence on Vitamin C Bioavailability and Capacity to Protect Against Ischemia Reperfusion Injury" Nutrition and Metabolic Insights Apr. 29, 2016.

\* cited by examiner

PREPARATION METHOD OF FATTY ACID LIPOSOME FOR VC ENCAPSULATION

TECHNICAL FIELD

The present disclosure relates to preparation method of fatty acid liposomes for VC encapsulation, and belongs to the field of pharmaceutical preparations.

BACKGROUND

Vitamin C (VC), also known as L-ascorbic acid, is a main component of common food additives and cosmetics, and can serve as a vitamin supplement and an antioxidant in cosmetics. However, VC is very unstable in neutral or alkaline aqueous solutions. As shown in FIG. 1, when having an initial concentration of 0.27 mg/mL in deionized water at 25° C., VC degrades by 29% after 12 h; and after being stayed in the deionized water for 6 h at a temperature higher than 50° C., VC can have a degradation rate of 80%.

Thus, the storage stability of VC is a problem that needs to be solved. In order to enhance the storage stability of VC, a technology of VC encapsulation with various wall materials, such as polysaccharides, proteins, polyethylene or polyethylene glycol, and various liposomes comes into being.

Liposomes are closed systems formed spontaneously by amphiphilic molecules dispersed in aqueous solutions, and the most typical one is composed of natural phospholipids and cholesterol, which has good biocompatibility and degradability and is often used to encapsulate bioactive substances. VC encapsulation with liposomes has been reported many times. For example, Farhang et al. (Farhang, 2012) prepare phospholipid nanoemulsion liposomes using a microjet technology, which has an embedding efficiency of 26% against ascorbic acid. Yang Shuibing et al. (Yang, 2010) prepare VC liposomes by taking lecithin and cholesterol as membrane materials (total lipid:VC=25:1) and using a film-ultrasound technique, which can have an encapsulation efficiency of 42.1% under the optimum condition. Bao Shibao et al. (Bao, 2013) prepare a VC nano-liposome suspension in a 0.05 mol/L Na2HPO4-KH2PO4 buffer salt at a pH of 6.5 by means of an ethanol injection method and by taking lecithin and cholesterol as membrane materials (total lipid:VC=5:2), which has a VC encapsulation efficiency of 71.4%.

In addition to the above traditional liposomes, there are polysaccharide modified liposomes. For example, Zou Xuekun et al. (Zou, 2017) enable a novel polymer carrying system by means of interaction of two polysaccharides (chitosan and sodium alginate) via static electricity and by making the two polysaccharides self-assembled and modified on surfaces of the traditional liposomes encapsulating VC in layers at a pH of 5.5. Zhang et al. (Zhang, 2019) prepare a maltodextrin ascorbic acid (dispersed phase) glass extrusion, a maltodextrin Arabic gum ascorbic acid (dispersed phase) glass extrusion, and a maltodextrin trehalose ascorbic acid (dispersed phase) glass extrusion by means of a hot-melt extrusion technology, wherein the glass-transition temperatures (Tg) of all the extrusions are 40° C. or above, and ascorbic acid is evenly dispersed in a glass matrix.

In the above examples, the problems of VC encapsulation with liposomes is that the piece of raw materials such as lecithin and cholesterol that are used are high; preparation methods are complex, the steps are long and organic solvents are needed; and the encapsulation of VC with the liposomes above is mostly carried out in an environment with the pH being slightly neutral. However, VC is extremely unstable in an environment above neutral pH, and can only be encapsulated and stabilized under an acidic condition.

Therefore, it is necessary to provide a low-cost, easy-to-obtain and environment-friendly method to stabilize liposome capsule materials that encapsulate VC under the acidic condition.

Conjugated linoleic acid (CLA) is a homogeneous substance or mixture of various octadecadienoic acid isomers, which can not only naturally exist, but also be conjugated from plant-derived linoleic acid or gamma linoleic acid. CLA and other fatty acids have good compatibility with foods and cosmetics and are beneficial to human health, thus achieving double benefits by encapsulating VC with them. However, since both CLA and fatty acids can only be self-assembled to form liposome structures in an alkaline environment (pH 8.5±0.5), and liposomes formed by CLA itself are very small, the encapsulation efficiency is low. In order to encapsulate VC, it is particularly important to make the pH range of fatty acid liposomes migrate towards acidity and to increase the sizes of liposomes.

SUMMARY

Technical Problem

The technical problem to be solved by the present disclosure is that vitamin C is stable under an acidic condition, while an existing method for embedding vitamin C with liposomes needs to be carried out under a neutral or alkaline condition, which will destroy stability of vitamin C and cause a low encapsulation efficiency.

Technical Solution

The present disclosure provides a method for preparing fatty acid-based vitamin C liposomes. A complex of industrial conjugated linoleic acid and other fatty acids and sodium dodecyl sulfate is taken as a capsule material, which is self-assembled to embed vitamin C in an aqueous phase under an acidic condition to form the fatty acid-based vitamin C liposomes, wherein condensed molecular formulas of the other fatty acids conform to a general formula $C_nH_{2n+1}COOH$, where n is a positive integer greater than 7; and the method comprises the following steps:

(1) evenly mixing the industrial conjugated linoleic acid and the other fatty acids, adding an SDS aqueous solution accounting for 5% to 10% of total fatty acids by mass into the mixture, adjusting a pH of a self-assembled liquid to 3.5 to 4.0 with diluted acid, and homogenizing the self-assembled liquid to obtain a suspension; and (2) under a condition of stirring, dropwise adding a VC aqueous solution into the suspension obtained in step (1), and after completion of dropwise adding, shaking out the mixture at 20 to 50 rpm for 10 min to 1 h.

Fatty acids in a fatty acid base are organic acids each having a carbon number of 8 or above in various carboxyl-containing molecules contained in raw materials including the conjugated linoleic acid, the other fatty acids and the industrial conjugated linoleic acid. The other fatty acids are homogeneous or mixed fatty acids with condensed molecular formulas conforming to a general formula $C_nH_{2n+1}COOH$ or $C_nH_{2n}COOH$ or $C_nH_{2n-1}COOH$ or $C_nH_{2n-3}COOH$, where n is a positive integer greater than 7.

The industrial conjugated linoleic acid is a product obtained by means of alkali-catalyzed conjugation of food-grade industrial linoleic acid, the conjugated linoleic acid is a homogeneous substance or mixture of various octadecadienoic acid isomers, and the total octadecadienoic acid isomers account for 70% to 100% of a dry matter of the industrial conjugated linoleic acid (calculated with percentages of gas chromatographic peak areas).

The other fatty acids account for 1% to 40% of total octadecadienoic acid isomers by mass.

A sum of final concentrations of fatty acids in the self-assembled liquid is 10 to 500 mM.

Added SDS accounts for 5% or 10% of the total fatty acids by mass.

After the completion of dropwise adding, a final concentration of VC in a suspension system is 1 to 50 mg/mL.

In alternative implementations of the disclosure, the fatty acids are self-assembled at 5 to 50° C. for 10 min to 2 h and encapsulate VC.

Beneficial Effects

VC is very unstable in neutral or alkaline aqueous solutions. The present disclosure provides a method for preparing fatty acid-based VC liposomes in acidic water. Materials that are used have good biocompatibility, the process is simple, and the raw materials are easy to obtain.

According to the disclosure, by adding sodium dodecyl sulfate (SDS) into fatty acids, the forming range of fatty acid liposomes is broadened, which can not only make the pH of liposomes formed by CLA migrate towards an acidic environment, but also can make the pH of liposomes formed by other fatty acids migrate towards the acidic environment, so that CLA and the other fatty acids can be self-assembled to form the liposomes to encapsulate VC under an acidic condition.

According to the disclosure, by adding a certain amount of the other fatty acids, especially saturated fatty acids, the size of the liposomes can be enlarged, and the encapsulation efficiency can be improved. Moreover, the higher the saturation degree of the added other fatty acids is, the larger the particle diameters of the formed liposomes are.

In addition to VC encapsulation under the acidic condition, the fatty acid-based liposomes prepared by the disclosure can play a role in slowly releasing VC.

A carrier fatty acid used in the disclosure is itself one of the essential fatty acids of a human body. The synergistic effect with VC can better promote the absorption of both. The carrier fatty acid can be used in foods or cosmetics. Moreover, the disclosure does not use organic solvents and other substances harmful to the human body in the preparation process, and has the characteristics of safety and health.

DETAILED DESCRIPTION

Figure 1:
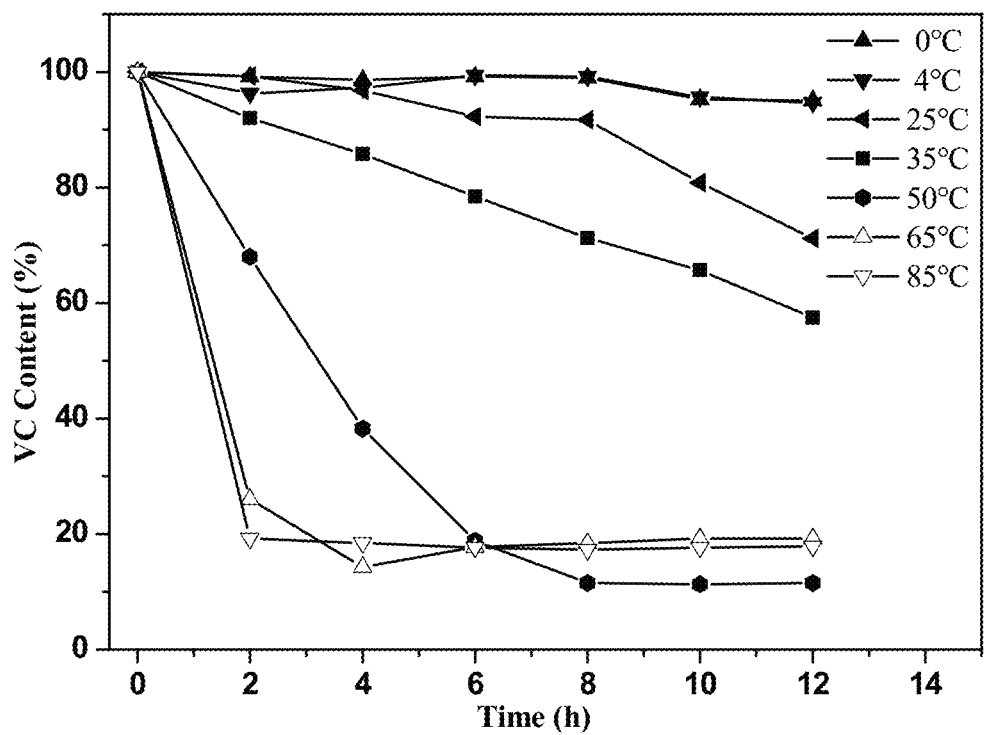
FIG. 1 shows changes of VC mass percentages over time in a VC aqueous solution at different temperatures.

Analytical Method:

1. Determination of fatty acid compositions in CLA: detection of a methyl ester derivative thereof using gas chromatography. Determination of fatty acids in foods according to GB5009.168-2016 National Food Safety Standard (gas chromatography internal standard method): 8 ml of a 2% sodium hydroxide methanol solution was added into 0.2 g of CLA, and the mixture was connected with a reflux condenser to be subjected to reflux on a water bath at 80° C.±1° C. until oil drops disappeared; 7 mL of a 15% boron trifluoride methanol solution was added from the upper end of the reflux condenser, and the mixture continued being subjected to reflux on the water bath at 80° C.±1° C. in 2 min; the reflux condenser was flushed with a small amount of water, heating was stopped, and a flask was removed from the water bath and quickly cooled to the room temperature; 10 mL to 30 mL of n-heptane was accurately added into the flask and shaken out for 2 min, and a saturated sodium chloride aqueous solution was added for still-standing layering; about 5 mL of a n-heptane supernatant extracting solution was sucked and transferred into a 25 mL test tube, about 3 g to 5 g of anhydrous sodium sulfate was added, the mixture was shaken out for 1 min and subjected to still standing for 5 min, and a supernatant solution was sucked into a sample bottle to wait for determination. Chromatographic conditions: a) capillary chromatographic column: polydicyanopropyl siloxane strong-polar stationary phase, column length 100 m, inner diameter 0.25 mm, and film thickness 0.2 µm. b) sample injector temperature: 270° C. c) detector temperature: 280° C. d) temperature programming: initial temperature 100° C., and duration 13 min; heating to 180° C. at a rate of 10° C./min for 6 min; heating to 200° C. at a rate of 1° C./min for 20 min; heating to 230° C. at a rate of 4° C./min for 10.5 min. e) carrier gas: nitrogen. f) split ratio: 100:1. g) injection volume: 1.0 µL. h) detection conditions should meet the theoretical plate number (n) of at least 2000/m and resolution (R) of at least 1.25.

A fatty acid standard determination solution and a to-be-determined sample were respectively injected into a gas chromatograph under the above chromatographic conditions, and the content of each of the fatty acids was quantitatively calculated with peak areas of chromatographic peaks.

2. Morphology characterization of fatty acid-based VC liposomes: characterization using TEM images. A copper grid was clamped by tweezers and immersed in a fatty acid-based VC liposome dispersion liquid having a concentration of 10 mM for 2 s, the copper grid was quickly taken out and frozen in liquid nitrogen, then the copper grid was transferred into a freezer dryer for drying for 24 h, and the morphology of the fatty acid-based VC liposomes on the copper grid was observed using a TEM (120 kV) and photographed.

3. VC encapsulation efficiency and slow release rate: VC (L-ascorbic acid) aqueous solutions having certain concentration intervals and a concentration range of 2 to 30 µg·mL$^{-1}$ were respectively prepared, the absorbance ($A_{260}$) of the corresponding solutions at 260 nm was measured, and concentration-absorbance standard curves of the VC aqueous solutions were drawn.

5 mL of a fatty acid-based VC liposome solution was placed into a dialysis bag (MW3500), the dialysis bag was placed into a 250 mL beaker loaded with 200 mL of deionized water, and the solution was stirred at 25° C. for dialysis. In the meantime, a VC solution with the same final concentration as the fatty acid-based VC liposome solution was used as a control sample. After dialysis for 1 h, the VC concentration of the control sample was balanced with that of a dialysis medium (200 mL of deionized water), which could be assumed that free VC in the fatty acid-based VC liposome sample had also been dialyzed out. At this moment, the absorbance ($A_{260}$) of a solution outside the dialysis bag of the fatty acid-based VC liposome sample at 260 nm was measured, and the concentration of VC in the solution outside the dialysis bag was calculated using the concentration-absorbance standard curves of the VC aqueous solutions. The difference between the amount of VC that was used in preparation of the fatty acid-based VC liposome and the mount of free VC released by dialysis was the amount of encapsulated VC. Therefore, in the fatty acid-based VC liposomes, the encapsulation efficiency (EE) of the fatty acid liposomes to VC could be calculated using the following formula.

$$\text{Encapsulation efficiency } (wt\ \%) = \frac{m_1 - m_2}{m_1} \times 100\%$$

$m_1$ was the amount of VC in the initial dialysis bag where the fatty acid-based VC liposomes were located (i.e., the amount of VC used in the preparation of 5 mL of fatty acid-based VC liposomes); and $m_2$ was the amount of VC in the solution outside the dialysis bag after dialysis for 1 h.

The above fatty acid-based VC liposome which was dialyzed for 1 h was placed into another 250 mL beaker loaded with 200 mL of fresh deionized water or a buffer solution for dialysis, at regular intervals, 3 mL of a solution was taken out from a dialysis solution outside the dialysis bag, the absorbance of 3 mL of the solution on an ultraviolet spectrophotometer at 260 nm was immediately measured, and an equal volume of fresh dialysis solution (deionized water or buffer solution) was timely supplemented into the beaker. The amount of VC released from the fatty acid-based VC liposomes could be calculated by determining the content of VC in the dialysis solution outside the dialysis bag, thus calculating the cumulative release rate of VC in the fatty acid-based VC liposome. The calculation formula was as follows.

$$\text{Cumulative release rate } (\%) = \frac{c_n \times V_0 + \sum_{i=1}^{n-1} (c_i \times V_s)}{m} \times 100\%$$

$C_n$ and $C_i$—the concentration of VC in the dialysis solution outside the dialysis bag at nth sampling, $n \geq 1$;

$V_0$—the volume of the dialysis solution outside the dialysis bag at the beginning of VC release;

$V_s$—the volume at each sampling; and m—the mass of VC in the fatty acid-based VC liposomes.

In the following examples, fatty acid compositions (wt %) of 95% industrial CLA include 93.5% of total octadecadienoic acid isomers, 3.7% of oleic acid, 0.7% of palmitic acid, 0.4% of stearic acid and 1.7% of linoleic acid, where the average molecular weight of CLA is 278.73. Fatty acid compositions (wt %) of 80% industrial CLA include 81.1% of total octadecadienoic acid isomers, 9.8% of oleic acid, 5.3% of palmitic acid, 2.5% of stearic acid and 1.3% of linoleic acid, wherein the average molecular weight of CLA is 278.71.

EXAMPLE 1

VC Liposomes Prepared from Palmitic Acid-CLA-SDS

Step (I)

At 60° C., 0.1 g of palmitic acid and 1.3 g of 95% industrial CLA (with an average molecular weight of 278.73) were evenly mixed, and the mixed CLA-palmitic acid was added into 250 mL of an SDS aqueous solution (having a mass concentration of 0.056% and containing 0.14 g of SDS) to be easily and evenly mixed so as to obtain a mixture system. The pH of the mixture system was adjusted to be 3.5 using diluted hydrochloric acid, and after homogenizing, a suspension was obtained.

Step (II)

250 mL of a 2 mg/mL VC aqueous solution was dropwise added into the above suspension while stirring was carried out at 25° C. and 150 rpm, and dropwise adding of the VC aqueous solution was completed within 30 min; and the mixed solution dropwise added with VC was shaken out at 50 rpm and 25° C. for 30 min.

Figure 2:
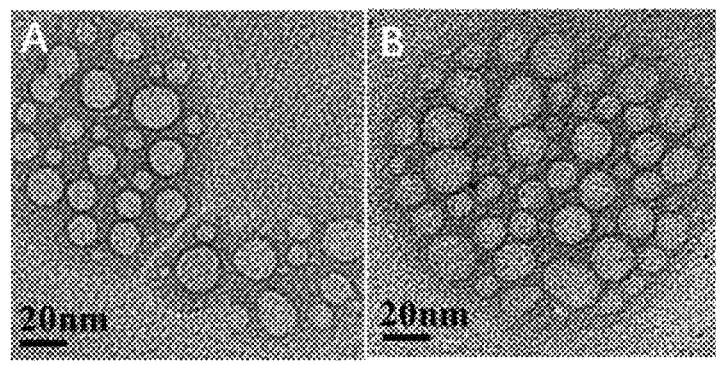
FIG. 2 shows TEM images of fatty acid-basedVC liposomes, (A): palmitic acid-CLA-VC, and (B): palmitic acid CLA-VC.

In an obtained fatty acid-based VC liposome solution, fatty acids had a concentration of 10 mmol/L, and VC had a concentration of 1 mg/mL. The encapsulation efficiency of VC was determined to be 53.5%. The morphology of the obtained VC liposomes was shown as FIG. 2A.

Comparative Example 1

Replacement of SDS with Deionized Water, and Other Conditions being the Same as Example 1

Step (I)

At 60° C., 0.1 g of palmitic acid was added into 1.3 g of 95% industrial CLA (with an average molecular weight of 278.73) to be evenly mixed. The mixed CLA-palmitic acid was added into 250 mL of a deionized water solution to be easily and evenly mixed so as to obtain a mixture system. Then, the pH of the mixture system was adjusted to be 3.5 using diluted hydrochloric acid, and after homogenizing, a suspension was obtained.

Step (II)

250 mL of a 2 mg/mL VC aqueous solution was dropwise added into the above suspension while stirring was carried out at 25° C. and 150 rpm, and dropwise adding of the VC aqueous solution was completed within 30 min, so that in the mixed system containing VC, fatty acids had a final concentration of 10 mmol/L, VC had a concentration of 1 mg/mL. The mixed system containing VC was shaken out at 50 rpm and 25° C. for 30 min. After completion of shaking out, the mixed system was observed with a microscope, and the observation results showed that no fatty acid formed liposome at this moment, thus there being no encapsulated VC.

Comparative Example 2

Replacement of SDS with Nonionic Surfactant Tween 80, and other Conditions being the same as Example 1

Step (I)

At 60° C., 0.1 g of palmitic acid and 1.3 g of 95% industrial CLA (with an average molecular weight of 278.73) were evenly mixed, and the mixed CLA-palmitic acid was added into 250 mL of a Tween 80 aqueous solution (having a mass concentration of 0.255% and containing 0.637 g of Tween 80) to be easily and evenly mixed so as to obtain a mixture system. Then, the pH of the mixture system was adjusted to be 3.5 using diluted hydrochloric acid, and after homogenizing, a suspension was obtained.

Step (II)

250 mL of a 2 mg/mL VC aqueous solution was dropwise added into the above suspension while stirring was carried out at 25° C. and 150 rpm, and dropwise adding was completed within 30 min. The mixed system containing VC was shaken out at 50 rpm and 25° C. for 30 min.

After completion of shaking out, the mixed system was observed with a microscope, and the observation results showed that no fatty acid formed liposome at this moment, thus there being no encapsulated VC.

If, in step (I), the pH of the mixture system was adjusted to be 7.4 or 6.0, the liposomes could be formed, and encapsulation efficiencies of VC were 23.6% and 29.7%, respectively. Comparative example 3 Replacement of SDS with anionic surfactant CLA-Na, and other conditions being the same as Example 1

Step (I)

At 60° C., 0.1 g of palmitic acid and 1.3 g of 95% industrial CLA (with an average molecular weight of 278.73) were evenly mixed, and the mixed CLA-palmitic acid was added into 250 mL of a CLA-Na aqueous solution (having a mass concentration of 0.056% and containing 0.014 g of CLA-Na) to be easily and evenly mixed so as to obtain a mixture system. Then, the pH of the mixture system was adjusted to be 3.5 using diluted hydrochloric acid, and after homogenizing, a suspension was obtained.

Step (II)

250 mL of a 2 mg/mL VC aqueous solution was dropwise added into the above suspension while stirring was carried out at 25° C. and 150 rpm, and dropwise adding was completed within 30 min. The mixed solution containing VC was shaken out at 50 rpm and 25° C. for 30 min.

After completion of shaking out, the mixed system was observed with a microscope, and the observation results showed that no fatty acid formed liposome at this moment, thus there being no encapsulated VC.

EXAMPLE 2

VC Liposomes Prepared from Palmitic Acid-CLA-SDS

Step (I)

At 60° C., 1 g of palmitic acid and 13 g of 95% industrial CLA (with an average molecular weight of 278.73) were evenly mixed, and 250 mL of an SDS aqueous solution (having a mass concentration of 0.56% and containing 1.4 g of SDS) was added into the mixed CLA-palmitic acid to be easily and evenly mixed so as to obtain a mixture system. Then, the pH of the mixture system was adjusted to be 3.5 using diluted hydrochloric acid, and after homogenizing, a suspension was obtained.

Step (II)

250 mL of a 10 mg/mL VC aqueous solution was dropwise added into the above suspension while stirring was carried out at 25° C. and 150 rpm, and dropwise adding was completed within 30 min. The mixed system containing VC was shaken out at 30 rpm and 25° C. for 90 min.

In an obtained fatty acid-based VC liposome system, fatty acids had a concentration of 100 mmol/L, and VC had a concentration of 5 mg/mL. The encapsulation efficiency of VC was determined to be 64.1%. The morphology of the fatty acid-based VC liposomes was shown as FIG. 2B.

Compared with Example 1, it could be seen that the increase of fatty acid concentration could improve the encapsulation efficiency of VC.

EXAMPLE 3

VC Liposomes Prepared from Palmitic Acid-CLA-SDS

Step (I)

At 60° C., 1 g of palmitic acid and 13 g of 95% industrial CLA were evenly mixed, and 250 mL of an SDS aqueous solution (having a mass concentration of 0.56% and containing 1.4 g of SDS) was added into the mixed CLA-palmitic acid to be easily and evenly mixed so as to obtain a mixture system. Then, the pH of the mixture system was adjusted to be 3.8 using diluted hydrochloric acid, and after homogenizing, a suspension was obtained.

Step (II)

250 mL of a 10 mg/mL VC aqueous solution was dropwise added into the above suspension while stirring was carried out at 25° C. and 150 rpm, and dropwise adding was completed within 30 min. The mixed solution was shaken out at 20 rpm and 20° C. for 50 min. In an obtained fatty acid-based VC liposome system, fatty acids had a concentration of 100 mmol/L, and VC had a concentration of 5 mg/mL. The encapsulation efficiency of VC was 66.5%.

Compared with Example 1, it could be seen that the increase of carbon number of saturated fatty acids could slightly increase the size of a self-assembled body, which was conducive to the increase of VC encapsulation efficiency.

EXAMPLE 4

VC Liposomes Prepared from Palmitic Acid-Stearic Acid-CLA

Step (I)

0.1 g of mixed palmitic acid-stearic acid (with a mass ratio of 1:1) was added into 1.3 g of 80% industrial CLA (with an average molecular weight of 278.71), and palmitic acid-stearic acid-CLA was shaken out at 60° C. and 120 rpm for 60 min. Then, 250 mL of an SDS aqueous solution (having a mass concentration of 0.056% and containing 0.14 g of SDS) was added into the above mixed fatty acid sample to be easily and evenly mixed so as to obtain a mixture system. Then, the pH of the mixture system was adjusted to be 3.8 using diluted hydrochloric acid, and after homogenizing, a suspension was obtained.

Step (II)

250 mL of a 10 mg/mL VC aqueous solution was dropwise added into the above suspension while stirring was carried out at 25° C. and 150 rpm, dropwise adding was completed within 30 min, and the mixed solution was shaken out at 25° C. and 50 rpm for 60 min.

In an obtained fatty acid-based VC liposome system, fatty acids had a concentration of 10 mmol/L, and VC had a concentration of 5 mg/mL. The encapsulation efficiency of VC was 58.4%.

As could be seen, the decrease of total octadecadienoic acid isomers in CLA could reduce the encapsulation efficiency of VC.

EXAMPLE 5

Slow Release of VC in Fatty Acid-CLA-VC

When fatty acid-based VC liposomes were used in medicines, there was a certain time requirement for slow release of VC in the VC liposomes. When the fatty acid-based VC liposomes were used in cosmetics, the slower the release was, the better the effect was. Since the slow release of VC in a cream state could not be determined, this example carried out dialysis analysis on the slow release of VC in the different fatty acid-based VC liposomes using universal aqueous media.

Figure 3:
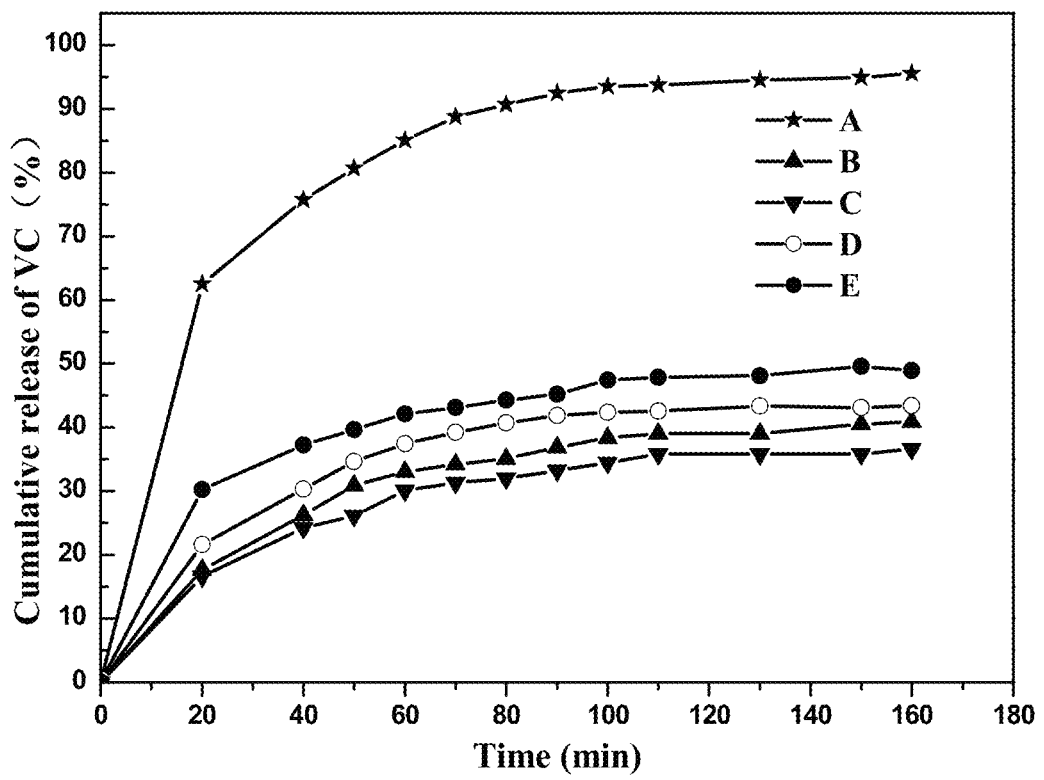
FIG. 3 shows VC release curves of VC aqueous solution-based and mixed fatty acid-based VC liposomes in water, (A): 1 mg/mL VC aqueous solution, (B): palmitic acid-CLA (10 mM)-VC (1 mg/mL) liposome, (C): palmitic acid-CLA (100 mM)-VC (2 mg/mL) liposome, (D): stearic acid-CLA (100 mM)-VC (5 mg/mL) liposome, and (E): palmitic acid-stearic acid-CLA (10 mM)-VC (5 mg/mL) liposome.

After complexing of different fatty acids with 95% CLA, the slow release condition of VC in the fatty acid-based VC liposomes prepared by referring to a process of the above example was subjected to dialysis analysis using the universal aqueous media. The results were shown as FIG. 3, after dialysis for 160 min, the cumulative release rate of VC in a control sample (1 mg/mL VC aqueous solution) was 95.5%, the cumulative release rate of VC in stearic acid-CLA (100 mM)-VC (5 mg/mL) liposomes prepared in Example 3 was 43.2%, and the cumulative release rate of VC in palmitic acid-CLA (100 mM)-VC (2 mg/mL) liposomes prepared according to a method identical to Example 3 was 36.5%, indicating that fatty acids with short carbon chains tended to delay the release of VC. The release rate of VC in the palmitic acid-CLA (10 mM)-VC (1 mg/mL) liposomes prepared in Example 1 was 40.9%, indicating that CLA at a low concentration accelerated the release of VC; while the cumulative release rate of VC in palmitic acid-stearic acid-CLA (10 mM)-VC (5 mg/mL) prepared in Example 4 was 48.9%, which was because the concentration potential energy of VC at a high concentration accelerated the release of VC.

EXAMPLE 6

VC Skin Cream Prepared from Fatty Acid-Based VC Liposomes

Palmitic acid-CLA (100 mM)-VC (2 mg/mL) liposomes which were released most slowly were taken and used to prepare a VC skin cream according to the following formula and process.

Preparation of an oil phase: 5 g of monoglyceride, 1 g of mink oil, 15 g of sterol, 2 g of *Centella asiatica*, a 50% ethanol extract and 5 g of liquid paraffin were evenly mixed at 60° C. to obtain the oil phase;

Preparation of an aqueous phase: 5 g of glycerol and 2 g of ginsenoside (50% gypenosides) were dissolved in 50 ml of deionized water, and finally, 5 mL of palmitic acid-CLA (100 mM)-VC (2 mg/mL) liposomes were added into the mixture to be evenly mixed so as to obtain the aqueous phase;

After mixed, the oil phase and the aqueous phase were homogenized at 6000 r/min for 7 min for degasification; An essence with a mass percentage of 0.3% and a preservative with a mass percentage of 0.2% were added at 50° C., the mixture continued to be cooled and stirred to a room temperature, and after degasification, the VC skin cream was obtained.

By replacing 5 mL of palmitic acid-CLA (100 mM)-VC (2 mg/mL) liposomes in the above formula with 5 mL of a VC solution (2 mg/mL), a control sample of VC skin cream made using the VC solution was prepared according to the same process.

100 g of the VC skin cream prepared from the fatty acid-based VC liposomes and 100 g of the VC skin cream prepared from the VC solution were taken respectively and aseptically loaded into five 30 mL sample bottles respectively (20 g in each bottle), and the sample bottles were capped and placed into an incubator at 37° C. for accelerated oxidation. The VC skin cream prepared from the fatty acid-based VC liposomes showed no color change and was not layered after being placed for three months. Samples of the VC skin cream prepared from the VC solution were not layered after placed for three months, but the color turned yellow after one month and was deepened over time.

The raw material of industrial conjugated linoleic acid used in the above Examples is a commercially available commodity, which can be purchased from INNOBIO, HISEA and other companies.

Although the disclosure has been disclosed above as preferable examples, they are not used to define the disclosure, and any of those skilled in the art may make various changes and modifications without departing from the spirit and scope of the disclosure. Therefore, the scope of protection of the disclosure shall be defined in the claims.

What is claimed is:

1. A method for preparing fatty acid-based vitamin C (VC) liposomes, which comprises:
   mixing food-grade linoleic acid and other fatty acids to make a mixture,
      wherein condensed molecular formulas of the other fatty acids conform to a general formula $C_nH_{2n+1}COOH$, wherein n is a positive integer greater than 7,
      wherein the food grade linoleic acid is a product obtained by alkali-catalyzed conjugation of food-grade industrial linoleic acid to make conjugated linoleic acid,
      wherein the conjugated linoleic acid is a homogeneous substance or mixture of various octadecadienoic acid isomers, and
      wherein the total octadecadienoic acid isomers account for 70% to 100% of a dry matter of the food grade linoleic acid by mass,
   adding an sodium dodecyl sulfate (SDS) aqueous solution accounting for 5% to 10% of total fatty acids by mass into the mixture to create a complex of the linoleic acid and the other fatty acids with SDS to form a capsule material, wherein the capsule material is a self-assembled liquid, wherein a sum of final concentrations of fatty acids in the self-assembled liquid is 10 mM to 500 mM,
   adjusting a pH of the self-assembled liquid to 3.5 to 4.0 with diluted acid,
   homogenizing the self-assembled liquid to obtain a suspension adding dropwise a VC aqueous solution while stirring into the suspension to embed VC thereby forming the fatty acid-based VC liposomes, and shaking the mixture at 20 rpm to 50 rpm for 10 minutes to 1 hours.

2. The method of claim 1, wherein the food grade linoleic acid and the other fatty acids form a fatty acid base that are organic acids each having a carbon number of 8 or above.

3. The method of claim 1, wherein the other fatty acids account for 1% to 40% of total octadecadienoic acid isomers by mass.

4. The method of claim 2, wherein the other fatty acids account for 1% to 40% of total octadecadienoic acid isomers by mass.

5. The method of claim 1, wherein a final concentration of VC in the fatty acid-based VC liposomes is 1 mg/mL to 50 mg/mL.

6. The method of claim 1, wherein the SDS accounts for 5% or 10% of the total fatty acids by mass.

7. A fatty acid-based VC liposome prepared by the method of claim 1.

* * * * *